US006312911B1

(12) United States Patent
Bancroft et al.

(10) Patent No.: US 6,312,911 B1
(45) Date of Patent: Nov. 6, 2001

(54) DNA-BASED STEGANOGRAPHY

(76) Inventors: Frank Carter Bancroft, 51 Dewey St., Huntington, NY (US) 11743; Catherine Clelland, 324 E. 59th St., Apt. 4A, New York, NY (US) 10022

( * ) Notice: Subject to any disclaimer, the term of this patent is extended or adjusted under 35 U.S.C. 154(b) by 0 days.

(21) Appl. No.: 09/566,796

(22) Filed: May 5, 2000

Related U.S. Application Data

(60) Provisional application No. 60/138,175, filed on Jun. 8, 1999, and provisional application No. 60/132,738, filed on May 6, 1999.

(51) Int. Cl.[7] .................................................... C12Q 1/68
(52) U.S. Cl. .................................................................... 435/6
(58) Field of Search ........................................................ 435/6

(56) References Cited

U.S. PATENT DOCUMENTS 6,167,518 * 12/2000 Padgett et al. ................. 713/186

OTHER PUBLICATIONS

Clelland, C.T. et al., "Hiding messages in DNA microdots", Nature, vol. 399, pp. 533–534 (1999).*

* cited by examiner

Primary Examiner—Kenneth R. Horlick
Assistant Examiner—Teresa Strzeckla

(57) ABSTRACT

The present invention relates to a stenographic method for concealing coded messages in DNA. The method of the invention comprises concealing a DNA encoded message within a genomic DNA sample followed by further concealment of the DNA sample to a microdot. The present invention further provides a method for the use of genomic steganography to mark and authenticate objects of interest.

16 Claims, 4 Drawing Sheets

ENCRYPTION KEY

| | | | |
|---|---|---|---|
| A=CGA | K=AAG | U=CTG | 0=ACT |
| B=CCA | L=TGC | V=CCT | 1=ACC |
| C=GTT | M=TCC | W=CCG | 2=TAG |
| D=TTG | N=TCT | X=CTA | 3=GCA |
| E=GGC | O=GGA | Y=AAA | 4=GAG |
| F=GGT | P=GTG | Z=CTT | 5=AGA |
| G=TTT | Q=AAC | =ATA | 6=TTA |
| H=CGC | R=TCA | ,=TCG | 7=ACA |
| I=ATG | S=ACG | .=GAT | 8=AGG |
| J=AGT | T=TTC | :=GCT | 9=GCG |

DNA-BASED STEGANOGRAPHY

This application claims priority to U.S. Provisional Application No. 60/138,175 filed on Jun. 8, 1999 and U.S. Provisional Application No. 60/132,738 filed on May 6, 1999.

INTRODUCTION

The present invention relates to a steganography method for concealing coded messages in DNA. The method of the invention comprises concealing a DNA encoded message within a genomic DNA sample followed by further concealment of the DNA sample to a microdot. The present invention further provides a method for the use of genomic steganography to mark and authenticate objects of interest.

BACKGROUND OF INVENTION

Steganography is a method of achieving confidentiality of a transmitted secret message by hiding the message inside of a larger context. The secret message is hidden in such a way that someone who is not supposed to read the message does not know how to read it, and in fact does not even know it is present; but someone who is supposed to read the message possesses a key that permits him/her to detect and read the message. (1996, David Kahn, The Codebreakers by Scribner).

A steganographic technique, referred to as the "microdot" was developed by Professor Zapp in Dresden and was employed by German spies in World War II to transmit information about U.S. "atom-kernel energy" utilization (Hoover, J. E., 1946, Reader's Digest 48:1–6). Such a microdot, considered "the enemy's masterpiece of espionage," was a greatly reduced photograph of a typewritten page, pasted over a period in an innocuous letter. By enlargement of the microdot, the secret message could be read.

There are a number of companies and associated patents describing macromolecular marking of objects. For example, Biocode Ltd (Cambridge, Mass.) employs antibody-antigen reactions (see U.S. Pat. No. 5,776,713). However, the technology revealed in the patent has, for many applications, a surprisingly low signal-to-noise ratio of perhaps 2:1–4:1.

There are also a number of patents describing DNA-based marking. However, the technologies to date employ nucleic acids labeled with agents that emit a signal when exposed to infrared radiation and DNA hybridization techniques. For example, DNA Technologies, Inc (www.dnatechnologies.com) apparently employs the labeling technique for marking (WO 99/34984), while U.S. Pat. No. 5,139,812 to Bioprobe Systems (Paris, France) describes a DNA hybridization technique for marking valuable objects.

SUMMARY OF THE INVENTION

The present invention relates to a steganographic method for concealing coded messages in DNA. The method of the invention comprises concealing a DNA encoded message within a genomic DNA sample followed by further concealment of the DNA sample to a microdot. The present invention further provides for the use of genomic stenography to mark and authenticate objects of interest. The present invention takes advantage of the great complexity of the genome of an organism to hide a secret message in the genomic DNA.

DETAILED DESCRIPTION OF THE INVENTION

The present invention relates to a method for concealing coded messages within a DNA sample. The present invention further relates to the use of such a method in conjunction with DNA array technology to provide a novel authentication technique that can be performed readily and conveniently.

Figures 1A, 1B:
FIG. 1A. Genomic steganography. Structure of a prototypical secret message DNA strand. Abbreviations: F, Forward, R, Reverse.
FIG. 1B. Key employed to encode a message in DNA.

A prototypical secret message DNA strand contains an encoded message flanked by PCR primer sequences as presented in FIG. 1B. The insignificant role of encryption in steganography permits use of a simple substitution cipher to encode characters in DNA triplets. Since the human genome contains c. $3 \times 10^9$ nucleotide pairs per haploid genome, human DNA fragmented and denatured to physically resemble secret message DNA would provide a very complex background for concealment of secret message DNA. For example, a 100 nucleotide long secret message DNA added to treated human DNA to one copy per haploid genome would be hidden in a c. three million-fold excess of physically similar, but informationally heterogenous human DNA strands. Confinement of such a sample to a microdot might then permit concealment from an adversary of even the medium containing the message. However, the intended recipient, knowing both the secret message DNA PCR primer sequences, the encryption key, and the location of the microdot, could readily amplify the secret message DNA, and then read and decode the message.

An adversary, having somehow detected such a microdot, would still experience extreme difficulty in reading the message without knowing the specific primer sequences. For example, use of 20-base random primers to amplify the secret message DNA would require, even permitting three mismatches per primer, separate amplifications with >$10^{20}$ different primer pairs, and analysis of any PCR products obtained. Similar considerations apply to attempts to shotgun clone the DNA sample and analyze resultant clones. Thus, even if the same primer pair were used on multiple occasions, discovery by an adversary of the primer sequences would be an extreme experimental barrier. Support for this assertion from farther mathematical and biochemical analysis would show that the primer pairs employed in this technique are not analogous to a classic single-use cryptographical "one-time pad" (1996, David Kahn, The Codebreakers by Scribner).

Attempted use by an adversary of a subtraction technique to detect the secret message DNA concealed within human DNA could be parried by using as background a random mixture of genomic DNAs of different organisms- The intended recipient could still employ the present procedures to amplify and read the secret message DNA, even if ignorant of the random mixture composition; and even if the primers proved to amplify artifactually a limited number of genomic sequences, since the encryption key would reveal which PCR product encodes a sensible message. The present technique would also permit use of a single or duplicate microdots to send individual secret messages to each of a number of intended recipients, who would each employ a unique set of primers to amplify only his/her intended message.

In experiments described herein, microdots containing 100 copies of secret message DNA per human haploid genome, that had been attached via common adhesives over periods in a printed letter and posted through the U.S. mail, yielded the correct PCR amplification product. The present technique might thus find utility similar to the original microdots: enclosure of a secret message in an innocuous missive. Scale-up of the encoded message from the size of the simple example we have executed should be possible, perhaps by encoding a longer message in multiple smaller DNA strands. It also seems quite feasible to scale down the sizes of the microdots employed. Such very small DNA-containing dots might find application in multiple areas, including both cryptography and specific tagging of a property of interest.

Transmission of A Coded Message Within DNA

The present invention relates to methods for concealing a DNA encoded message within a highly complex DNA sample. In a further embodiment of the invention, the DNA encoded message may be incorporated into ink for use in printing. In a preferred embodiment any convenient method for encoding a secret message may be employed to encode a secret message into DNA. For example, a simple three-base code to represent each letter of the alphabet may be used; e.g., the three-base sequences AAA, AAC, AAG, and CCC might represent, respectively, the alphabet letters A, B, C and D.

The message encoded in the DNA is flanked on either end by primer sequences known only to the sender and the intended recipient of the message. The DNA sequence corresponding to the secret message plus its flanking primer sequences is referred to herein as a "secret DNA molecule". The secret DNA molecule can be synthesized by conventional techniques well known to those of skill in the art, preferably in double-stranded form, but possibly alternatively in single-stranded form, yielding a DNA molecule of the form illustrated in FIG. 1A. As presented in FIG. 1A the secret DNA molecule consists of a DNA fragment containing a coded message, flanked by a 5' primer sequence (labeled Primer-1) and a 3' primer sequence (labeled Primer-2). In a preferred embodiment of the invention, the size of the primer sequences are between 15–20 base-pairs in length, thereby minimizing the chances of non-specific priming from a DNA sequence(s) present in the concealing DNA employed.

In an embodiment of the present invention, the synthetic secret DNA sequence is single-stranded, although in some cases it may prove preferable to use PCR to convert the synthetic secret DNA sequence to a double-stranded form, and then hide this in double-stranded genomic DNA that has been fragmented, but not denatured. Individual secret single-stranded oligodeoxynucleotide sequences, of defined length (e.g. 100 mers) are hidden by adding them to genomic DNA from an appropriate organism or mixtures of organisms, to a level just sufficient to yield a detectable signal following primer extension (possibly on the order of 0. 1–1.0 oligodeoxynucleotide copies per haploid genome). The genomic DNA can be from any individual species (human would probably be preferable) or any combination of species (e.g., human, yeast, fly, bacteria, etc.). The presence of the genomic DNA would cause all samples to appear identical by conventional DNA staining techniques.

In addition various methods may be employed to better conceal the secret DNA within the genomic DNA thereby preventing detection of the secret DNA by an unintended recipient. For example, biochemical modifications of the DNA may be introduced into the secret DNA to make it appear more similar to the concealing DNA while preserving the ability of the secret DNA to serve as a carrier of an encrypted message, or for authentication of a product. Because human DNA contains regions of methylated CdG, the secret DNA may be methylated prior to mixing with the concealing DNA. Further, repetitive sequences such as Alu repeats or simple tetra-,tri- or di- nucleotide repeats, may be incorporated into the secret DNA to appear more like genomic DNA. Incorporating such repeats into the secret DNA would prevent the use of subtractive hybridization techniques for identification and reading of the secret DNA. In addition, terminal phosphorylation or dephosphorylation may be carried out to produce both secret DNA and concealing DNA fragments with indistinguishable 3' or 5' terminal phosphorylation states.

The synthetic secret DNA may also be detected by an unintended recipient based on the presence of blocking groups that remaining attached to the secret DNA following synthesis. Thus, in another embodiment of the invention, the blocking groups may be removed from the secret DNA using methods well known to those skilled in the art. Alternatively, the synthetic DNA may be PCR-amplified prior to use which would result in removal of the blocking groups during amplification.

In addition, the secret DNA molecules may be identified based on the expectation that all the secret DNA molecules would be precisely the same length. To generate secret DNA molecules differing in size but all possessing the same primer sequences required for either PCR amplification or primer extension, the primer sequences may be flanked by random oligonucleotide sequences of various random lengths. For example, such random oligonucleotide sequences may be ligated to the ends of the central primer sequences.

In addition, "nucleic acid" molecules other than DNA may be used to transmit a secret message. By "nucleic acid" is meant any nucleic acid, whether composed of deoxyribonucleosides or ribonucleosides, and whether composed of phosphodiester linkages or modified linkages. The term nucleic acid also specifically includes nucleic acids composed of bases other than the five biologically occurring bases (adenine, guanine, thymine, cytosine, and uracil). In some circumstances, as where increased nuclease stability is desired, nucleic acids having modified internucleoside linkages may be preferred. Nucleic acids containing modified internucleoside linkages may also by synthesized using reagents and methods that are well known in the art.

Once synthesized, the secret message DNA molecule is hidden within a concealing DNA sample. The concealing DNA may be, for example, genomic DNA or random synthetic DNA. In a specific embodiment of the invention, genomic DNA can be isolated from any convenient source species, for example, from human genomic DNA, believed to contain approximately three billion base-pairs per haploid genome. In a preferred embodiment this genomic DNA is fragmented (e.g., by shearing) to an average size approximately equal in size to the secret message DNA molecule, thus yielding a vast background of similarly-sized DNA molecules in which the secret message is hidden.

Figure 2:
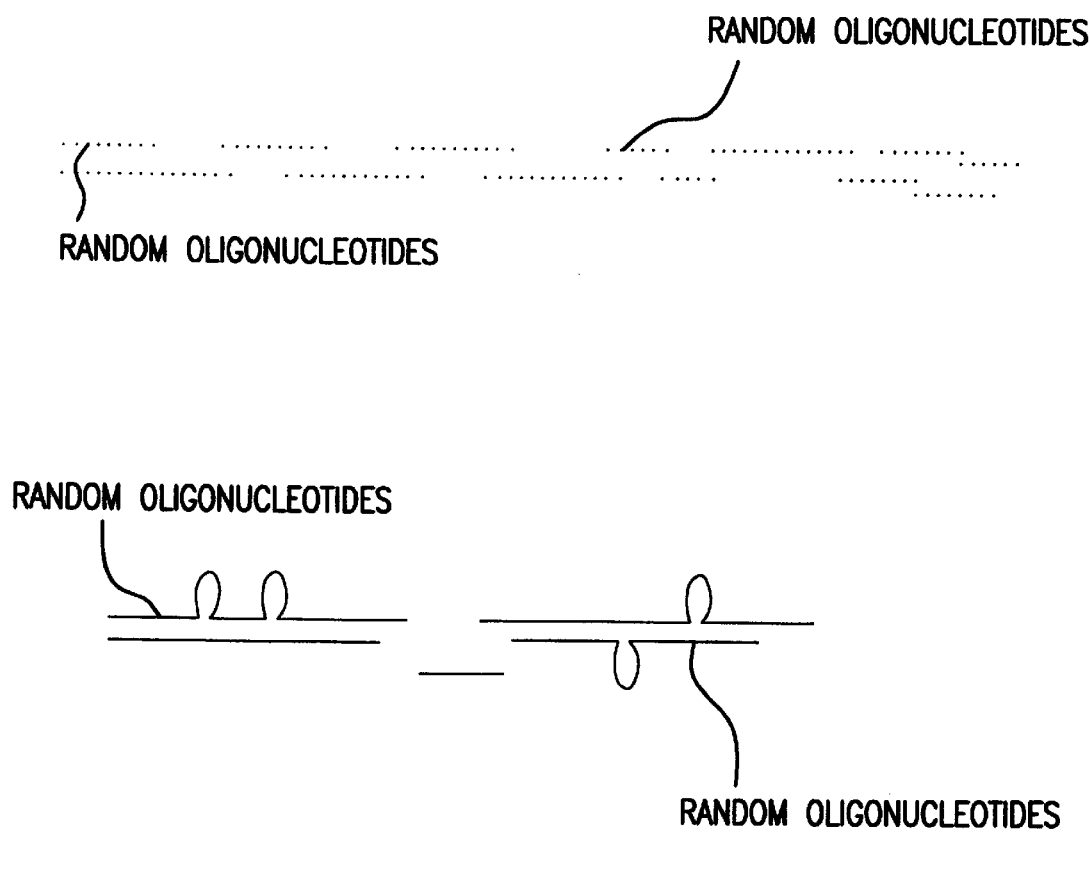
FIG. 2. Synthesis of Random Synthetic DNA. A random collection of oligonucleotides are hybridized slowly under conditions designed to yield heterodimers. The appropriate enzymes are used to fill in the gaps yielding double-stranded DNA molecules. Ligase is then used to blunt-end ligate the molecules together.

Alternatively, random synthetic DNA may be generated for use as a concealing DNA sample. To prepare synthetic DNA, a random collection of oligonucleotides are hybridized slowly under conditions designed to yield heterodimers. Such hybridization conditions will generate random structures such as those depicted in FIG. 2. Using the appropriate enzymes, e.g., DNA polymerases such as T4 polymerase, gaps between the hybridized heterodimers are filled to form double-stranded DNA molecules. Ligase is then added to blunt-end ligate the molecules together thereby forming a random assortment of molecules. Finally, to generate random-sized fragments of DNA in a quantity that can be used in genomic stenography, PCR amplification is performed using a mixture of the original oligonucleotides that were used as primers. If desired, the resultant amplified random synthetic DNA may be size selected to yield a population of synthetic double-stranded DNA that is approximately the same size as the secret DNA.

The secret message is hidden simply by adding an appropriate number of copies (perhaps 10–50) of the secret DNA molecule to each genome or synthetic equivalent of DNA. This collection of DNA molecules is herein referred to as a "secret DNA molecule hidden in DNA."

The secret DNA molecule can be recovered and read by the intended recipient, but not by an adversary (i.e., a person attempting to intercept, detect and read the secret message), using the following method. Using sequences of the DNA that are present on the 5' and 3' ends of the secret DNA molecule, DNA oligonucleotides that are capable of priming a DNA extension reaction are constructed, followed by the performance of a standard polymerase chain reaction (PCR) reaction to specifically amplify the secret DNA molecule. The resultant amplified DNA band can then be detected by standard techniques (e.g., gel electrophoresis) and recovered. The DNA may then be cloned and or directly sequenced by standard techniques (e.g., DNA sequence analysis), yielding the sequence of the message in the DNA. The original encoding scheme can then be reversed to read the original secret message. Using such a technique, an adversary will not be able to read the secret message because the adversary does not know the sequences of the primer sequences present on the ends of the secret DNA molecule, and thus will not be able to perform PCR to amplify the secret DNA molecule.

Moreover, the adversary will not even know that the secret DNA molecule bidden in DNA contains a secret message, since, in the absence of PCR amplification, the secret DNA molecule will represent a trace contaminant of the genomic DNA, and hence will be difficult or impossible to detect. The implication of this ill the general context of cryptography is as follows: It might be thought at first that these primers represent what is termed in cryptography a "one-time pad", which can only be employed a single time to encode a message, and then must be discarded. However, if an adversary cannot even detect the presence of secret DNA molecule, then the adversary cannot employ analysis of the sequence of the secret DNA molecule to obtain information about the primers used to retrieve the secret DNA molecule. Additionally, the adversary also cannot obtain information about the encoding employed to encode the secret message in DNA. Thus, the sender and recipient of the message could potentially reuse the same two primers (known only to each of them) multiple times to transmit secret messages between them.

It is possible that an adversary might attempt to perform a "difference analysis" between normal genomic DNA from an organism (e.g., human) and genomic DNA from the same organism to which the secret DNA molecule has been added to detect a secret DNA molecule. By analyzing the difference between these two samples, the adversary might be able to detect and then decode the secret message. The potential for detection of the secret message can be readily avoided by putting copies of the secret DNA molecule into a mixture of genomic DNAs isolated from various sources, e.g., human, yeast, Drosophila, mouse, bacteria, plants, etc.

The proportions of genomic DNA from each organism could be arbitrary and variable for different secret messages, and it would not be necessary that the intended recipient (or even the sender) know the actual identities or proportions of genomic DNA from different organisms that are represented. Since the adversary would not know the identities or the ratios of the sources of the genomic DNAs employed, the adversary would thus be prevented from performing a "difference analysis".

In another embodiment of the invention, a number of secret messages could be added to the same genomic DNA background. In such an instance, each such secret message could be encoded in a message DNA flanked by a unique set of primer sequences, and the corresponding secret DNA molecule would thus be uniquely amplified by the corresponding unique primers. Each such secret message could in fact be intended for a different recipient. Each recipient would know the sequence of only one set of primers, and thus could amplify and decode only the single secret DNA molecule meant for that recipient.

Primers employed for amplification may amplify other DNA fragments in addition to the secret DNA molecule, possible because of priming of DNA sequences present in the genomic DNA employed. To prevent this, random primers could be pretested on the background DNA of choice, and only primers that yielded no detectable band employed in subsequent amplification steps. Alternatively, primer length and/or the stringency of priming can be increased to reduce PCR contaminants, or the input of secret DNA molecule can be increased to increase the probability that this molecule yielded the major PCR product. In addition, the multiple amplified bands obtained could be separated from each other (e.g., by gel electrophoresis). DNA sequence analysis and attempts to decode all such bands would then readily reveal which band corresponds to DNA containing a secret message that makes sense, thus permitting reading of the message. The ability to detect a PCR product that actually corresponds to a secret DNA molecule would be made somewhat easier if the total size of the secret DNA molecule were agreed on in advance by the sender and recipient of the message, since then only amplified bands of the correct size would need to be further analyzed.

In yet another embodiment of the present invention genomic stenography could be used to label commercially valuable transgenic organisms; e.g., plants that have been modified by genetic engineering. A secret DNA molecule could be inserted into the genome of such an organism, which would contain a message in DNA identifying the company that produced the transgenic plant. The presence of the message in DNA would not be apparent to anyone who did not know the sequences of the primer sequences in the secret DNA molecule. However, if an organism were suspected of having been obtained illegally from the company that owned the rights to it, the company could simply obtain a sample of the suspect organism, isolate genomic DNA, and then employ the primers known only to the company to PCR amplify the secret DNA molecule. The company could then read the sequence of the "message in DNA", and thus demonstrate its ownership of the transgenic organism.

Genetic Steganography as A Method for Marking and Authenticating Objects of Interest The present invention provides for the use of genetic steganography to mark and authenticate objects of interest, or indeed anything requiring authentication. Such a technique may be used to mark various kinds of documents, including, for example, printed documents, currency or fashion apparel.

Alternatively, the object may be marked indirectly by attachment of a tag marked with secret DNA. Such tags may be composed of any number of different substrates including but not limited to paper, glass, plastic, nitrocellulose, nylon or fabric.

In a specific embodiment, such tags may be used to authenticate fashion apparel, and thus prevent counterfeiting. Various types of apparel tags previously used for this purpose have generally suffer from the problem that unauthorized persons can copy and produce counterfeit tags for use in authenticating "counterfeit" goods. In contrast, secret DNA marking cannot be duplicated, and can only be read by someone authorized to do so. For authentication of fashion apparel, only a sample of the goods present in a shipment need be authenticated, whereas more frequent authentication may be required in other applications.

Authentication may be based on the identification of a coded message in the secret DNA used to mark the object requiring authentication. In such instances, a standard polymerase chain reaction is performed to specifically amplify the secret DNA molecule. The DNA may then be directly sequenced by standard techniques, yielding the coded message in the DNA thereby authenticating the object. Alternatively, to avoid the need for sequencing of DNA, a number of secret DNA molecules of differing lengths may be used to mark the object. A PCR reaction performed in the presence of the appropriate primers will result in the amplification of secret DNA molecules of the expected lengths thereby authenticating the marked object. To determine whether fragments of the expected lengths have been amplified, the PCR amplified fragments may be separated using, for example, polyacrylamide gel electrophoresis.

In a preferred embodiment of the invention, the approach described above for concealing coded messages within a DNA sample may be combined with current DNA chip technology to provide a novel authentication technique that can be performed rapidly and conveniently.

The technology of micro array fabrication known as DNA chip technology can provide small, densely packed two-dimensional arrays of individual DNA sequences (see, e.g., Bothwell, D. D. L., 1999, Nature Genetics Supplement 21:25–32). For example, up to 300,000 different DNA oligodeoxynucleotide sequences can be synthesized in-situ on 1.28 cm×1.28 cm arrays (Affymetrix). Although these oligodeoxynucleotides are currently in the range of 20–25 mers, this length can be increased. Alternatively, microscope slide dot arrays of immobilized complementary DNA's, 100–50 $\mu$m in diameter with 200–250 $\mu$m separating the center of each dot, have been manufactured in the range of 6000 per 1"×3" area (Incyte).

In an embodiment of the present invention, a two-dimensional DNA array is constructed, and a given short synthetic secret DNA sequence (perhaps 50–100 nucleotides in length) is denatured and added only to certain dots in the array, such that these dots form a certain pattern. Detection of this unique pattern then represents the authentication of the product. In order to conceal information about which dots received this secret DNA sequence, genomic DNA from a single or multiple organisms is also added to each dot, so that, as with the genomic steganography procedure described above, the primer is present at about one copy per genomic DNA equivalent. In an embodiment of the invention, a complex mixture of synthetic DNA may be substituted for the genomic DNA. To read this pattern, one round of primer extension (i.e., not PCR) is carried out according to standard techniques, in the presence of labeled dNTP's, employing a short (c. 20 base) primer sequence complementary to the 3' end of the secret DNA sequence. The use of fluorescent tags to label the dNTP's is preferred, but other commonly employed labels such as radioactively labeled dNTPs could also be used. Since primer extension would incorporate the label into a DNA strand that is already immobilized, the incorporated label would also be immobilized, and thus would not diffuse into solution.

Reading the resultant fluorescent pattern should be well within currently available technology. However, if primer extension did not prove to yield a sufficiently strong signal, the readout could be done by employing several rounds of PCR, using primers corresponding to the two ends of the secret DNA sequence, as described above.

The result of this readout represents two levels of authentication. First, the detection of a primer extension product in any of the dots authenticates the product. Second, the product is further authenticated only if the result of primer extension yields the appropriate pattern. As described in detail below, this pattern can encode a specific number so that e.g., the serial number displayed on currency can be authenticated by the pattern yielded by primer extension.

These samples are placed, as described above, in two-dimensional addressable arrays of small "dots", arrayed on or in the object to be marked. Multiple areas or dots, each containing a specified species or population of secret DNA sequence (i.e., oligodeoxynucleotides or "templates"), can be attached either covalently or non covalently, or they can be placed on, or within the object, as part of a capsule, container or device, itself attached to, or held within the object.

When groups of DNA-dots, each of which contain none, one or more, different oligodeoxynucleotide templates, are arrayed two-dimensionally on an object, the pattern of the dots will itself be usable for holding information in a coded form. For example, if only a fraction of the dots in the micro-array contained oligodeoxynucleotide template, then this would form a pattern of dots containing the oligodeoxynucleotide. This dot pattern would be detectable only following primer extension. On the basis of analogous studies involving mutation detection using nested genetic bit analysis (see, e.g., Head, S. R., Nucleic Acids Research 25:5065–5071, 1997) one round of primer extension might be expected to be sufficient for detection of a specific signal.

The resultant fluorescent dot pattern would be analyzed using procedures analogous to those currently employed following DNA hybridization to DNA microarrays (see, e.g., Schena, M., et al., 1995, Science 270:467–470).

Dots containing oligodeoxynucleotide templates should become fluorescent following primer extension and removal of excess unincorporated dNTP's, while dots containing background genomic DNA alone should exhibit considerably lower levels of fluorescence. However, as noted above, in order to detect a specific signal, it may be necessary to employ several rounds of PCR in place of primer extension, using primers corresponding to the two ends of the secret DNA sequence. In that case, it would be necessary to retain the PCR products on the surface on which they are produced, to avoid diffusion of these products in solution and the resultant cross contamination between dots. This could be achieved by placing the two-dimensional addressable arrays of dots described above upon a matrix carrying a cationic charge. This matrix could either be directly incorporated into the object to be marked, or could be attached to said object. This matrix could be composed of any of numerous anion-exchange resins commonly employed in molecular biology techniques; for example, the material in the DNA purification column available from Qiagen (Qiagen Plasmid Purification Handbook, 1997).

During PCR amplication, some of the anionic DNA molecule products would be expected to bind to the anion-exchange resin on the matrix, and thus remain affixed to the dot where they were produced. However, in order to avoid an artifactual signal over negative dots, arising from PCR products that were actually formed over positive dots, it might be necessary to modify the technique to perform separate PCR reactions over each dot in the matrix. Subsequent washes of the matrix with low/medium salt solution would then remove primers and labeled deoxynucleotide triphosphates that had not been incorporated into PCR products, and the signal resulting from PCR could be read as described above. Finally, use of the present technology is not limited to primer extension or PCR as described here, since this technology could readily incorporate any technique that employs a nucleic acid as a template to produce a number of labeled copies (e.g., transcription, reverse transcription, DNA or RNA replication, etc.).

The resultant pattern could then be "read" employing techniques currently employed for standard DNA microarrays (see, e.g., Cheung, V. G., et al, "Making and reading microarrays", Nature Genetics Supplement 21:15–19). Thus the technique should thus lend itself to automation and would be a quick and convenient method of identifying objects, since the primer extension step would require only annealing and extension.

In order to decode an encoded pattern, a user would have to know both the precise sequence of the secret DNA added to some of the dots, or at least of a primer sequence that could extend that sequence; and the pattern to expect following either a primer extension or PCR amplification. The chances are vanishingly small that an unauthorized person, not possessing this information, could obtain by random manipulations of the microarray, the correct fluorescent pattern.

The present technique is expected to be more specific than hybridization techniques, simply because, with short primers, the specificity of extension is greater than the specificity of hybridization. This has the added advantage that our technique permits the use of genomic DNA for concealing the secret DNA identification molecules, while this would be very difficult with hybridization, because of problems arising from non-specific hybridization; and no redundancy needs to be built into the chip array, as is currently necessary with current hybridization- based chip techniques.

The present invention may be used to mark and authenticate printed documents or paper currency. However, this approach could be readily extended to marking and authenticating virtually any item of interest. The technique described here could be readily modified to mark and authenticate other flat items, including but not limited to credit cards, various recording media (CD's, DVD's, laser discs, etc.) paintings, material in clothing, tags attached to clothing, collectors items such as telephone cards, etc. In addition, solid, three-dimensional items could be similarly marked and authenticated, including but not limited to such specific items as valuable baseballs, industrial parts, jewelry, pottery, antique furniture etc.

This technique could readily be applied to marking and authenticating precious liquids such as high-grade oil or gasoline, wines or other liquors, pharmaceuticals (in either liquid or solid form), and perfume. In that case, it would probably not be useful to employ a DNA micro-array for authentication. Instead, the liquid would receive from the manufacturer a small sample containing a known quantifiable amount of genomic DNA plus the secret DNA oligodeoxynucleotide sequence described above. Authentication would then consist of carrying out PCR analysis as described above on a small aliquot of the liquid, but in this case employing quantitative PCR amplification and determination of whether any PCR product(s) obtained contain, at the expected level, the same sequence as the added secret DNA oligodeoxynucleotide. If this result were obtained it would show that the original fluid was genuine. Use of this type of quantitative assay should prevent counterfeiters from attempting to claim that genuine liquid that had been diluted with counterfeit liquid is actually pure, unadulterated genuine liquid.

In yet another embodiment of the invention, the present technique could also be employed to authenticate hand-written documents or signatures, or more generally any document produced by application of ink to a surface, by incorporating the DNA mixture described above directly into the ink employed for preparation of such documents or signatures, followed by analysis of the ink-containing portion of the document, essentially as described in Section II above for analysis of DNA-containing microdots.

In an embodiment of the invention, an important, possibly diplomatic, document would be received from the sender containing a small array of dots immobilized in a specified location on its surface. For a recipient to authenticate the document, the document would be placed into a machine programmed to perform primer extension, using the primers agreed upon in advance by sender and recipient. After removal of excess dNTPs, the same or another machine would scan the dot array to detect the fluorescent emission from the now double-stranded DNA molecules in the dots. If the pattern of dots which "lights up" during scanning encoded the expected pattern, the document would be identified as genuine.

For a given document, following detection as above, the primer extension or PCR products could readily be removed by employing appropriate, commonly employed denaturing solutions (see, e.g., Unit 2.10 of Short Protocols in Molecular Biology, Ausubel, F., et al, Eds. Third Edition, Wiley and Sons, 1995). This would both leave fewer traces on the document of the authenticity test, and also permit such a test to be carried out repeatedly on the same document. If the document is marked by a particular company, that same company will probably have to authenticate the document, since only that company will probably know the sequence of the secret DNA and expected pattern to be obtained following analysis as described above.

Analogous procedures could be applied to authentication of paper currency. In that case, the expected pattern of dots that "light up" could encode a number that corresponds to the serial number printed on the currency. Other uses for this procedure could easily be found, for authenticating clothes, charge cards of various kinds, and other valuable objects.

Example: A Secret DNA Message is Concealed in A Genomic DNA Sample

The subsection below describes the preparation and mailing of DNA microdots containing a secret DNA molecule. The secret DNA molecule was successfully amplified to yield the coded message.

Materials and Methods

Design of encryption key and oligodeoxynucleotides. The encryption key was generated by the random number generator function in the Borland C++ compiler (v. 4.5), using a number between 1–4 to represent each base. Codons for each alphanumeric symbol were generated until each symbol was represented by a unique three-base DNA sequence. The forward and reverse primer sequences were selected from among a set of previously synthesized 20-base long oligodeoxynucleotides, each with a sequence that is random except for a single central six nucleotide restriction enzyme site. Two primers were selected on the basis of the following properties: comparison with known human gene sequences yielded low probability of priming on human genomic DNA, which was confirmed by preliminary experiments; low probability of secondary structure; and identical melting temperatures (65° C.). The sequences of the forward and reverse primers selected are, respectively 5'-TCCCTCTTCGTCGAGTAGCA-3' and 5'-TCTCATGTACGGCCGTGAAT-3'. A secret message (SM) DNA oligodeoxynucleotide was synthesized containing, from the 5-terminus, the forward primer sequence, an encoded message, and the complement of the reverse primer sequence.

Preparation and mailing of DNA microdots. A Fisher Sonic Dismembrator (Model 300) was employed to sonicate human genomic DNA for 40 min at full power. Gel analysis showed that this procedure yielded DNA fragments with a size range of about 50–150 base-pairs. DNA was then converted to single strands by heating (95° C., 10 min) and snap-cooling. Following addition to the human DNA on ice of secret message DNA strands to various final levels, 6 ul of each sample containing 225 ng DNA was pipetted onto a 16 point period that had been printed with an AppleLaserJet Pro printer onto Whatman 3MM filter paper. Following air drying, a 19-gauge hypodermic needle was employed to excised the filter-printed period.

To prepare DNA microdots to be mailed, 8 ul containing 300 ng treated human DNA plus 100 copies per haploid genome of Secret message DNA was pipetted over a period onto filter paper, and the period excised, all as above. The microdot was then attached over an identical period on a letter printed on printer paper, employing any of three commercially available emulsion products- Wet 'n' Wild Clear Nail Protector, 3M Photo Mount™ spray adhesive, or Avery Permanent Glue Stick—and the letter self-addressed and mailed. Upon receipt of the letter four days later, the microdots were pried off, and subjected to PCR analysis as described below, except that 40 cycles of anplification were employed. A product of the expected size was obtained following PCR amplification of microdots that had been attached with any of the above emulsion products.

Amplification and analysis of the secret message DNA. Amplification was carried out by adding a DNA microdot directly to PCR Ready to Go Beads (Promega) plus 25 pmoles of each primer, 4% (final concentration) fetal bovine serum, and $MgCl_2$ (final concentration 2 mM), followed by initial denaturation (94° C., 5 min), 35 cycles of PCR (94° C., 45 sec; 58° C., 45 sec; 72° C., 45 sec; and a final extension (72° C., 5 min). The products wer analyzed on a 2.5% Metaphor agarose gel. Where indicated, the resultant amplified band was then excised, subjected to phenol/chloroform extraction and ethanol precipitation, and cloned into the pCR-Script plasmid vector (Stratagene) according to the manufacturer's instructions, resulting in a polishing off of the 5'-terminal T of the amplification product. A T7 primer was then employed to sequence the insert on an ABI 377 automated sequencer.

Results

Figure 1C:
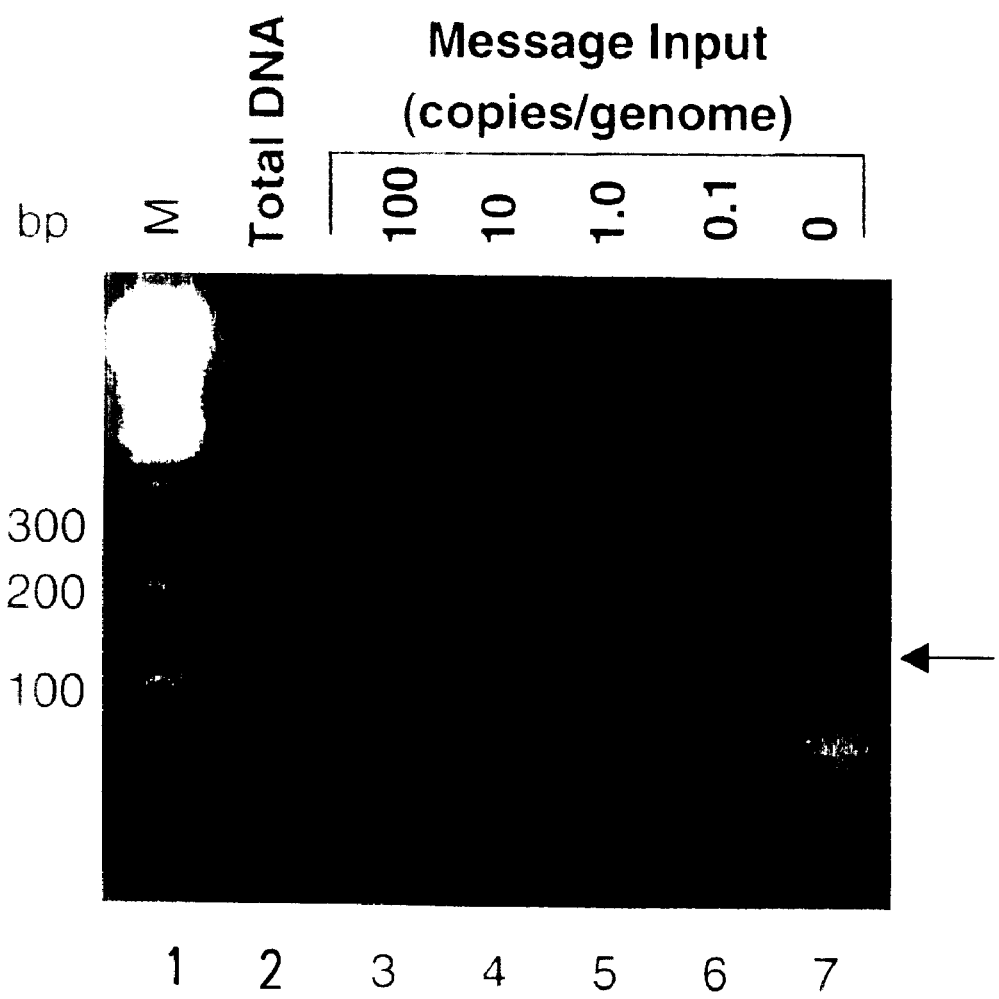
FIG. 1C. Gel analysis of products obtained by PCR amplification with specific primers of microdots containing secret message DNA strands hidden in a background of sonicated, denatured human genomic DNA. Message input in copies per human haploid genome is indicated, where 1.0 corresponds to 0.41 fg SM DNA in 11 ng human DNA. Lane 2 received a message input of 100, 20-fold more total DNA than the microdots, and was not PCR-amplified. M, 100 bp molecular weight markers. The gel was stained with ethidium bromide. Arrow indicates PCR product seen in some lanes, below which are seen primer-dimer bands.
Figure 1D:
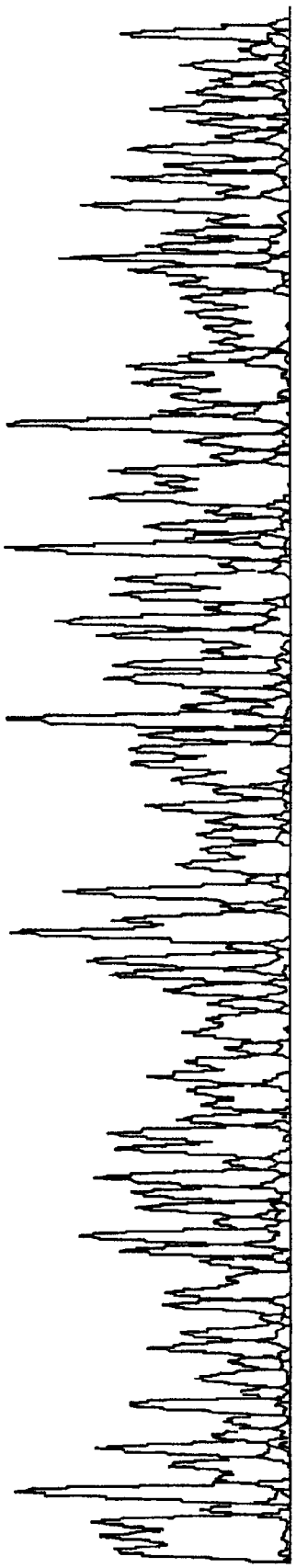
FIG. 1D. Sequence of the cloned product of PCR amplification, and outcome of use of the encryption key to decode the encoded message. Shown are the DNA sequence determined for the encoded message, and, in lower case, the flanking primer sequences obtained.

Concealing DNA physically similar to the single strands of secret message DNA was prepared by sonicating human DNA to roughly 50–150 nucleotide-pairs (average size), and denaturation. A 6 ul volume of each solution containing 225 ng treated human DNA, plus various amounts of added secret message DNA, was pipetted over a 16 point period printed on filter paper, finally occupying an area about 20-fold larger than the period. Excision of the printed periods, each containing about 10 ng DNA yielded DNA microdots. Sequences complementary to secret message DNA primers were employed to perform PCR directly on DNA microdots, without prior DNA solubilization (Clayton et al., 1998, Arch. Dis. Child 79:109–115), and the products analyzed by gel electrophoresis (FIG. 1C). An unamplified secret message DNA-containing sample yielded only a faint continuous smear (lane 2). By contrast, amplification of DNA microdots containing either 100, 10, or 1 Secret message DNA copies per haploid genome (lanes 3–5) each yielded a single product of the expected size (arrow). No such product was detected using microdots containing either 0.1 (lane 6) or 0 (lane 7) Secret message DNA copies per haploid genome, implying a present detection limit of about one Secret message DNA strand per haploid human genome. The amplified band in lane 4 of FIG. 1 (arrow) was excised, sub-cloned, and sequenced. Use of the encryption key (FIG. 1B) to decode the resultant DNA sequence (FIG. 1D) yielded the encoded text, containing probably the most significant secret of the original microdot era: "June6 Invasion:Normandy" (FIG. 1D).

The present invention is not to be limited in scope by the embodiments disclosed in the examples which are intended as an illustration of one aspect of the invention, and any compositions or methods which are functionally equivalent are within the scope of this invention. Indeed, various modifications of the invention in addition to those shown and described herein will become apparent to those skilled in the art from the foregoing description. Such modifications are intended to fall within the scope of the claims.

What is claimed:

1. A steganographic method for creation of a secret code comprising:
   (a) producing a DNA molecule comprising a secret message DNA sequence that can be decoded with the use of an encryption key, flanked on each side by a primer sequence; and
   (b) concealing the DNA molecule in a mixture of concealing DNA.

2. The method of claim 1 wherein the concealing DNA is genomic DNA.

3. The method of claim 2 wherein the genomic DNA is human DNA.

4. The method of claim 1 wherein the concealing DNA is synthetic.

5. A DNA molecule comprising a secret message DNA sequence that can be decoded with the use of an encryption key, flanked on each side by polymerase chain reaction primer sequences wherein amplification of the DNA molecule and determination of the secret message DNA sequence and use of an encryption key, results in a decoding of the message.

6. A method for genetic tagging of a non-human organism comprising introducing into said organism a DNA molecule comprising a secret message DNA sequence, that can be decoded with the use of an encryption key, flanked on each side by a polymerase chain reaction primers.

7. A method of authenticating an object of interest comprising:
   (a) adding at least one secret DNA molecule comprising a secret message DNA sequence flanked on each side by primer sequences to a mixture of concealing DNA;
   (b) attaching the mixture of secret DNA and concealing DNA to the object to be authenticated or a tag affixed thereto; and
   (c) detecting of the secret DNA;
      wherein detecting of the secret DNA authenticates the object of interest.

8. The method of claim 7 wherein the secret DNA is sequenced to determine the secret message DNA sequence.

9. The method of claim 7 wherein the concealing DNA is genomic DNA.

10. The method of claim 9 wherein the genomic DNA is human DNA.

11. A method of authenticating an object of interest comprising:
    (a) constructing a two dimensional array of DNA dots containing concealing DNA;
    (b) adding at least one secret DNA molecule to a subset of the DNA dots to form a pattern; and
    (c) detecting of the pattern of dots that contain secret DNA sequence as a means for authenticating the object of interest.

12. The method of claim 11 wherein the concealing DNA is genomic DNA.

13. The method of claim 12 wherein the genomic DNA is human DNA.

14. The method of claim 11 wherein the concealing DNA is synthetic.

15. A cell comprising a secret message DNA sequence, that can be decoded with the use of an encryption key, flanked on each side by a polymerase chain reaction primers.

16. A method for genetic tagging of a cell comprising introducing into said cell a DNA molecule comprising a secret message DNA sequence, that can be decoded with the use of an encryption key, flanked on each side by polymerase chain reaction primers.

* * * * *

SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 1
tccctcttcg tcgagtagca                                           20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide primer

<400> SEQUENCE: 2
tctcatgtac ggccgtgaat                                           20